United States Patent
Lappin et al.

(10) Patent No.: US 10,779,842 B2
(45) Date of Patent: Sep. 22, 2020

(54) METHOD USING COMBINATION REAMER/DRILL BIT FOR SHOULDER ARTHROPLASTY

(71) Applicant: DePuy Synthes Products, Inc., Raynham, MA (US)

(72) Inventors: Kyle E. Lappin, Fort Wayne, IN (US); Lieven De Wilde, Ghent (BE)

(73) Assignee: DePuy Synthes Products, Inc., Raynham, MA (US)

( * ) Notice: Subject to any disclaimer, the term of this patent is extended or adjusted under 35 U.S.C. 154(b) by 360 days.

(21) Appl. No.: 15/793,229

(22) Filed: Oct. 25, 2017

(65) Prior Publication Data

US 2018/0042621 A1 Feb. 15, 2018

Related U.S. Application Data

(62) Division of application No. 13/051,026, filed on Mar. 18, 2011, now Pat. No. 9,820,758.

(51) Int. Cl.
| | |
|---|---|
| *A61B 17/16* | (2006.01) |
| *A61B 17/17* | (2006.01) |
| *A61B 17/88* | (2006.01) |

(52) U.S. Cl.
CPC ...... *A61B 17/1684* (2013.01); *A61B 17/1778* (2016.11); *A61B 17/8872* (2013.01)

(58) Field of Classification Search
CPC ............ A61B 17/1684; A61B 17/1778; A61B 17/8872
See application file for complete search history.

(56) References Cited

U.S. PATENT DOCUMENTS

| | | | |
|---|---|---|---|
| 2,487,203 A | 11/1949 | Wilber | |
| 3,855,638 A | 12/1974 | Pilliar | |
| 4,030,143 A | 6/1977 | Elloy et al. | |
| 4,964,865 A | 10/1990 | Burkhead et al. | |
| 5,030,219 A | 7/1991 | Matsen, III et al. | |

(Continued)

FOREIGN PATENT DOCUMENTS

| | | |
|---|---|---|
| CH | 693446 | 8/2003 |
| EP | 1639949 A1 | 3/2006 |

(Continued)

OTHER PUBLICATIONS

Piasecki et al., Review Article: "Glenoid Bone Deficiency in Recurrent Anterior Shoulder Instability: Diagnosis and Management," JAm Acad. Ortho. Surg. 2009, vol. 17, pp. 482-493.

(Continued)

*Primary Examiner* — Kevin T Truong
*Assistant Examiner* — Tracy L Kamikawa
(74) *Attorney, Agent, or Firm* — Maginot, Moore & Beck, LLP

(57) ABSTRACT

A method of preparing a shoulder to receive a glenoid component in one embodiment includes accessing a glenoid of a shoulder, applying a rotational force to a combination device, forming a first bore in the glenoid with a rotating boring section of the combination device, forming a second bore in the glenoid at a location spaced apart from the first bore using a first drill guide defined by the combination device, and reaming a portion of the glenoid with a rotating reaming section of the combination device, wherein forming a first bore and reaming a portion of the glenoid occur at least partially simultaneously.

13 Claims, 10 Drawing Sheets

(56) References Cited

U.S. PATENT DOCUMENTS

| | | | |
|---|---|---|---|
| 5,080,673 | A | 1/1992 | Burkhead et al. |
| 5,180,384 | A | 1/1993 | Mikhail |
| 5,324,295 | A | 6/1994 | Shapiro |
| 5,489,310 | A | 2/1996 | Mikhail |
| 5,800,551 | A | 9/1998 | Williamson et al. |
| 5,919,195 | A | 7/1999 | Wilson et al. |
| 6,010,535 | A | 1/2000 | Shah |
| 6,045,302 | A | 4/2000 | Orr |
| 6,228,900 | B1 | 5/2001 | Shen et al. |
| 6,245,074 | B1 | 6/2001 | Allard et al. |
| 6,281,264 | B1 | 8/2001 | Salovey et al. |
| 6,364,910 | B1 | 4/2002 | Shultz et al. |
| 6,379,386 | B1 | 4/2002 | Resch et al. |
| 6,679,916 | B1 | 1/2004 | Frankle et al. |
| 6,699,289 | B2 | 3/2004 | Iannotti et al. |
| 6,783,549 | B1 | 8/2004 | Stone et al. |
| 7,294,133 | B2 | 11/2007 | Zink et al. |
| 7,329,284 | B2 | 2/2008 | Maroney et al. |
| 7,338,498 | B2 | 3/2008 | Long et al. |
| 7,604,665 | B2 | 10/2009 | Iannotti et al. |
| 8,764,836 | B2 | 7/2014 | De Wilde et al. |
| 2002/0082702 | A1 | 6/2002 | Resch et al. |
| 2003/0125809 | A1 | 7/2003 | Iannotti et al. |
| 2004/0097947 | A1 | 5/2004 | Wolford et al. |
| 2004/0193168 | A1 | 9/2004 | Long et al. |
| 2005/0278030 | A1 | 12/2005 | Tornier et al. |
| 2006/0020344 | A1 | 1/2006 | Shultz et al. |
| 2006/0069444 | A1 | 3/2006 | Deffenbaugh |
| 2006/0111787 | A1 | 5/2006 | Bailie et al. |
| 2006/0195194 | A1 | 8/2006 | Gunther |
| 2006/0276905 | A1 | 12/2006 | Calamel |
| 2007/0016304 | A1 | 1/2007 | Chudik |
| 2007/0038302 | A1 | 2/2007 | Shultz et al. |
| 2007/0055249 | A1 | 3/2007 | Jensen et al. |
| 2007/0251356 | A1 | 11/2007 | Tribby |
| 2007/0260321 | A1 | 11/2007 | Stchur |
| 2008/0306600 | A1 | 12/2008 | Huebner |
| 2009/0270993 | A1 | 10/2009 | Maisonneuve et al. |
| 2010/0070044 | A1 | 3/2010 | Maroney et al. |
| 2010/0087876 | A1 | 4/2010 | Gunther |
| 2010/0161065 | A1 | 6/2010 | Williams, Jr. et al. |
| 2010/0249938 | A1 | 9/2010 | Gunther et al. |
| 2010/0274359 | A1 | 10/2010 | Brunnarius et al. |
| 2010/0331990 | A1 | 12/2010 | Mroczkowski et al. |
| 2011/0012318 | A1 | 1/2011 | Northwood |
| 2011/0028977 | A1 | 2/2011 | Rauscher et al. |
| 2011/0035013 | A1 | 2/2011 | Winslow et al. |
| 2012/0130499 | A1 | 5/2012 | Long |
| 2013/0123930 | A1 | 5/2013 | Burt |

FOREIGN PATENT DOCUMENTS

| | | |
|---|---|---|
| EP | 1815825 | 8/2007 |
| FR | 2704747 | 11/1994 |
| FR | 2940607 | 7/2010 |
| GB | 2406278 | 3/2005 |
| JP | H1128256 | 5/1999 |
| JP | H11127256 | 5/1999 |
| JP | 2003230584 | 8/2003 |
| JP | 2009501026 | 1/2009 |
| JP | 2009518077 | 5/2009 |
| JP | 5123336 | 11/2012 |
| WO | 2010150223 | 12/2010 |
| WO | 2011005205 | 1/2011 |

OTHER PUBLICATIONS

Matsen III, Fredereick A., et al., " Shoulder Arthroplasty: The Socket Perspective," Journal of Shoulder and Elbow Surgery, Oct. 2007; 1: 24S-247S (7 pages).
Extended European Search Report corresponding to European Patent Application No. 16167719.0-1654, dated Sep. 6, 2016 (6 pages).
Australian Examination Report corresponding to application No. 2012231298, dated Sep. 17, 2015, (4 pages).
Chinese Search Report corresponding to application No. 201280023890.7, dated Jun. 5, 2015, (2 pages).
Japanese Office Action corresponding to application No. 2013-558132, dated Jan. 12, 2016 (5 pages).
Japanese Office Action corresponding to application No. 2014-501145, dated Jan. 19, 2016 (4 pages).
Chinese Search Report corresponding to application No. 201280023936.5, dated Aug. 25, 2015, (2 pages).
Chinese Supplementary Search Report corresponding to application No. 201280023936.5, dated Apr. 25, 2016, (2 pages).
Extended European Search Report corresponding to European Applicatoin No. 12760274.6, dated Jun. 27, 2014 (6 pages).
International Preliminary Report on Patentability corresponding to PCT application PCT/US2012/029034, dated Sep. 24, 2013 (7 pages).
Dictionary Definition for "best-fit", English Oxford Dictionaries Online, Accessed Oct. 3, 2016.
Dictionary Definition for "guide," English Oxford Dictionaries Online, Accessed Oct. 3, 2016.
Japanese Office Action con-esponding to application No. 2013-016623, dated Dec. 6, 2016 ( 4 pages).
International Search Report in corresponding PCT application (i.e. PCT/US2012/029021), dated Jul. 11, 2012 (4 pages).
Australian Examination Report No. 1 for AU application 2013200329, dated Aug. 18, 2017 ( 6 pages).
Jeske, H.C. et al., "Normal glenoid rim anatomy and the reliability of shoulder instability measurements based on intrasite correlation," Surg. Radiol. Anat. vol. 31, pp. 623-625, Mar. 2009 ( 3 pages).
Maisonobe et al,; Finding the Circle that Best Fits a Set of Points; Oct. 25, 2007 (11 pages).
Extended European Search Report corresponding to European Patent Application 12760666.3, dated May 13, 2014.
Extended European Search Report corresponding to European Patenit Application No. 12760199.5, dated Aug. 7, 2014 (6 pages).
Antuna et al., "Glenoid revision surgery after total shoulder arthroplasty," Journal of Shoulder Elbow Surgery, 2001, pp. 217-224, vol. 10, Rochester, MN (8 pages).
Boileau P, Walch G., "The three dimensional geometry of the proximal humerus. Implications for the surgical technique and prosthetic design." J. Bone Joint Surg Br 1997;79-B:857-65. doi:10.1302/0301-620X. 79B5. 7579 (9 pages).
Boyer P.J. Massimini DF, Gill TJ, Papannagari R, Stewart SL, Warner JP, Li G., "In vivo articular cartilage contact at the glenohumeral joint; preliminary report." J. Orthop Sci. 2008; 13:359-65. doi:10 1007/500776-008-1237-3 ( 7 pages).
Bryce CD, et al., "Two Dimensional glenoid version measurements vary with coronal and sagittal scapular rotation." J Bone Joint Surg Am. 2010;92-692-9 doi. 10 2106/JBJS. I.00177 ( 8 pages).
Codsi et al., "Normal glenoid vault anatomy and validation of a novel glenoid implant shape." Journal of Shoulder Elbow Surgery, May/Jun. 2008, pp. 471-478, vol. 17, Austria (9 pages).
Couteau B Mansat, et al., "Morphological and mechanical analysis of the glenoid by 3D geometric reconstruction using computed tomography." Clin Biomech 2000; 15 (suppl1): 8-12.doi:10. 1016/SO268-0033 (00)00052-8 ( 5 pages).
Couteau B, et al.,"Finite element analysis of the mechanical behavior of a scapula implanted with a glenoid prosthesis." Clin Biomech 2001: 16:566-75.doi: 10. 1016/S0268-033 (01)00029-8 (10 pages).
Couteau B, et al., "In vivo characterization of glenoid with use of computed tomography." J Shoulder Elbow Surg 2001; 116-22 (7 pages).
DeWilde LF, et al., "Reliability of the glenoid plane." J Shoulder Elbow Surg. 2010; 19:414-22. doi:10. 1016/j.jse.2009. 10.005. (9 pages).
Graichen H., et al., "Effece of abducting and adducting muscle activity on glenohumeral translation, scapular kinematics and subacromial space width in vivo." Journal of Biomechanics 2005; 38: 755-60. doi: 10. 1016/j.biomech.2004.05.020. (6 pages).
Graichen H., et al., "Glenohumeral translation during active and passive elevation of the shoulder—a 3D open-MRI study." Journal of Biomechanics 200;33:609-13.doi:10.10106/S0021-9290(99)00209-2. (5 pages).

(56) References Cited

OTHER PUBLICATIONS

Harryman, DT., et al., "The effect of articular conformity and the size of the humeral head component onlaxity and motion after glenohumeral arthroplasty." J. Bone Joint Surg Am 1995;77-A:555-63.No doi found. (10 pages).
Huysmans PE, et al., "The shape of the inferior part of the glenoid: a cadaveric study." J Shoulder Elbow Surg. 15(6): 759-63. doi: 10.1016/j.jse.2005.09.001 (5 pages).
Karelse, et al., "The Pillars of the Scapula," Clinical Anatomy, 2007, pp. 392-399, vol. 20, Belgium (8 pages).
Extended European Search Report corresponding to European Patent Application 12760666.3, dated May 13, 2014 (10 pages).
Extended European Search Report corresponding to European application No. 12760274.6, dated Jun. 27, 2014 (6 pages).
Japanese Office Action corresponding to application No. 2013-016623, dated Dec. 6, 2016 (4 pages).
Erichsen, "Injuries of the Nervous System on Railway and Other Injuries of the Nervous System", The Classic Article in Clinical Orthopaedics and Related Research, Mar. 1997, pp. 47-51, No. 458, Walton and Moberly, London (5 pages).
Iannotti JP, Gabriel JP, Schneck SL, Evans BG, Misra S., "The normal glenohumeral relationships. An anatomical study of one hundred and forty shoulders." J. Bone Joint Surg Am. 1992;74(4); 491-500. No doi found. (11 pages).
Karduna AR, Williams GR, Williams JL, Ianotti JP., "Glenohumeral Joint translations before and after total shoulder arthroplasty." J Bone Joint Surg 1997;79-A,1166-74. No doi found. (10 pages).
Lee SB, Kim KJ, O'Driscoll SW, Morrey BF, An KN., "Dynamic glenohumeral stability provided by the rotator cuff muscles in the mid-range and end-range of motion." A study in cadavera. J. Bone Joint Surg Am. 2000;82(6):849-57. No doi found (10 pages).
Lewis GS, Bryce CD, Davison AC, Hollenbeak CS, Piazza SJ, Armstrong AD., "Location of the optimized centerline of the glenoid vault: a comparison of two operative techniques with use of three-dimensional computer modeling." J Bone Joint Surg Am, 2010;92:1188-94. doi: 10-2106/JBJS.I.00131. (8 pages).
Mahfouz M, Nicholson G, Komistek R, Hovis D, Kubo M., "In vivo determination of the dynamics of normal, rotator cuff-deficient, total, and reverse replacement shoulders." J Bone Joint Surg Am. 2005;87 Suppl 2:107-13. doi:10.2106/JBJS.E.00483 (8 pages).
Massimini DF, Li G, Warner JP., "Glenohumeral contact kinematics in patients after total shoulder arthroplasty." J Bone Joint Surg Am. Apr. 2010;92(4):916-26. doi:10.2106/JBJS.H.01610. (12 pages).
Matsen FA., "Early effectiveness of shoulder arthroplasty for patients who have primary glenohumeral degenerative joint disease." J Bone and Joint Surg 1996;78-A:260-4. No doi found. (6 pages).
Nyffeler RW, Sheikh R, Atkinson TS, Jacob HA, Favre P, Gerber C., "Effects of glenoid component version on humeral lead displacement and joint reaction forces: an experimental study." J Shoulder Elbow Surg. 2006;15:625-9. doi:10.1016/j.jse.2005.09.016. (5 pages).
Nyffeler RW, Werner CM, Sukthankar A, Schmid MR, Gerber C., "Association of a large lateral extension of the acromion with rotator cuff tears." J. Bone Joint Surg Am. 2006;88-800-5. No doi found (7 pages).
Pappas GP, Blemker SS, Beaulieu CF, McAdams TR, Whalen ST, Gold GE, "In vivo anatomy of the Neer and Hawkins sign positions for shoulder impingement." J Shoulder Elbow Surg 2006;15:40-9. doi:10.1016/j.jse.2005.04.007. (10 pages).
Pearl ML, Krurtz S., "Geometric analysis of commonly used prosthetic systems for proximal humeral replacement." J Bone Joint Surg 1999;81-A:660-71. No doi found (13 pages).
Scalise JJ, Codsi MJ, Bryan J, Brems JJ, Iannotti JP., "The influence of three-dimensional computed tomography images of the shoulder in preoperative planning for total shoulder arthroplasty." J Bone Joint Surg Am. 2008;90:2438-45.doi:10.2106/JBJS.G.01341. (9 pages).
Schiffern SC, Rozencwaig R, Antoniou J, Richardson ML, Matsen FA III., "Anteroposterior centering of the humeral head on the glenoid in vivo." Am J Sports Med. 2002;30(3):382-7. No doi found. (7 pages).
Soslowsky LJ, Flatow EL, Bigliani LU, Pawluk RJ, Ateshian GA, Mow VC., "Quantitation of in situ contact areas at the glenohumeral joint: a biomechanical study." J Orthop Res. 1992;10:524-34. doi:10.1002/jor.1100100407. (11 pages).
Takase K, Yamamoto K, Imakiire A, Burkhead WZ Jr., "The radiographic study in the relationship of the glenohumeral joint." J Orthop Res. 2004;22:298-305. doi:10.1016/S0736-0266(03)00187-6 (8 pages).
Tokgoz N, Kanatli U, Voyvoda NK, Gultekin S, Bolukbasi S, Tali ET., "The relationship of glenoid and humeral version with supraspinatus tendon tears." Skeletal Radion. 2007;36:509-14. No doi found. (6 pages).
Werner CML, Weishaupt D, Blumenthal S, Curt A, Favre P, Gerber C., "Effect of experimental suprascapular nerve block on active glenohumeral translations in vivo." J Orthop Res 2006;24:491-500. doi:10.1002/jor.20011. (10 pages).
Bey, Michael J., et al., "Measuring Dynamic In-Vivo Glenohumeral Joint Kinematics: Technique and Preliminary Results," Journal of Biomechanics 41 (2008), pp. 711-714. (4 pages).
Chant, Chris B., et al., "Humeral Head Retroversion in Competitive Baseball Players and Its Relationship to Glenohumeral Rotation Range of Motion," Journal of Orthopaedic & Sports Physical Therapy, Sep. 2007, vol. 37, No. 9, pp. 514-520. (7 pages).
Conzen, Annemarie and Eckstein, Felix, MD, "Quantitative Determination of Articular Pressure in the Human Shoulder Joint," Journal of Shoulder and Elbow Surgery, vol. 9, No. 3, May/Jun. 2000, pp. 196-204. (9 pages).
De Wilde, Lieven F. MD, et al., "Glenohumeral Relationship in the Transverse Plane of the Body," Journal of Shoulder and Elbow Surgery, vol. 12, No. 3, May/Jun. 2003, pp. 260-267. (8 pages).
De Wilde, L.F., et al., "About the Variability of the Shape of the Glenoid Cavity," Surgical and Radiologic Anatomy (2004) 26; pp. 54-59. (6 pages).
Fleiss, Joseph L., "Analysis of Data From Multiclinic Trials," Controlled Clinical Trials 7: 267-275 (1986). (9 pages).
Hertel, Ralph M.D., "Geometry of the Proximal Humerus and Implications for Prosthetic Design," Journal of Shoulder and Elbow Surgery, Jul./Aug. 2002, vol. 11, No. 4, pp. 331-338. (8 pages).
Mansat, M. and Fourcade, D., "Preoperative Planning in Shoulder Prosthesis," Acta Orthopaedica Belgica (1995) vol. 61—Suppl. 1—1995. (6 pages).
Middernacht, Bart, MD, et al., "Consequences of Scapular Anatomy for Reversed Total Shoulder Arthroplasty,"Clinical Orthopaedics and Related Research (2008) 466: 1410-1418. (9 pages).
Moon, P. and Spencer, D.E., Rectangular Coordinates (x,y,z). Field Theory Handbook, Including Coordinate Systems, Differential Equations, and Their Solutions (1988), New York: Springer-Verlag, pp. 9-11 (Table 1.01). (3 pages).
Pearl, Michael L., M.D. and Volk, Albert G., M.D., "Coronal Plane Geometry of the Proximal Humerus Relevant to Prosthetic Arthroplasty," Journal of Shoulder and Elbow Surgery, vol. 5, No. 4, Jul./Aug. 1996, pp. 320-326. (7 pages).
Pearl, ML and Volk, AG, "Retroversion of the Proximal Humerus in Relationship to Prosthetic Replacement Arthroplasty," Journal of Shoulder and Elbow Surgery, Jul. 1995, vol. 4, No. 4, pp. 286-289. (4 pages).
Randelli, M., M.D. and Gambrioli, P.L., M.D., "Glenohumeral Osteometry by Computed Tomography in Normal and Unstable Shoulders," Clinical Orthopaedics and Related Research, No. 208, Jul. 1986, pp. 151-156. (6 pages).
Robertson, Douglas D., M.D., et al., "Three-Dimensional Analysis of the Proximal Part of the Humerus: Relevance to Arthroplasty," The Journal of Bone and Joint Surgery, vol. 82-A,No. 11, Nov. 2000, pp. 1594-1602. (9 pages).
Rougraff, Bruce T., M.D., et al., "Does Length of Symptoms Before Diagnosis of Sarcoma Affect Patient Survival?" Clinical Orthopaedics and Related Research (2007), No. 462, pp. 181-189. (9 pages).
Shrout, Patrick E. and Fleiss, Jospeh L., " Intraclass Correlations: Uses in Assessing Rater Reliability," Psychological Bulletin, 1979, vol. 86, No. 2, pp. 420-428. (9 pages).
Soslowsky, Louis J., Ph.D. et al, "Articular Geometry of the Glenohumeral Joint," Clinical Orthopaedics and Related Research, No. 285, Dec. 1992, pp. 181-190. (10 pages).

(56) References Cited

OTHER PUBLICATIONS

Tetreault, Patrice, et al., "Glenoid Version and Rotator Cuff Tears," Journal of Orthopaedic Research 22 (2004) pp. 202-207. (6 pages).
Warner, Jon J.P., M.D. et al, "Articular Contact Patterns of the Normal Glenohumeral Joint," Journal of Shoulder and Elbow Surgery, Jul./Aug. 1998, vol. 7, No. 4, pp. 381-388. ( 8 pages).
Westerhoff, P., et al., "In Vivo Measurement of Shoulder Joint Loads During Activities of Daily Living," Journal of Biomechanics 42 (2009), pp. 1840-1849. (10 pages).
Williams, Gerald R., Jr., M.D., and Iannotti, Joseph P., M.D. PhD., "Options for Glenoid Bone Loss: Composites of Prosthetics and Biologics," Journal of Shoulder and Elbow Surgery, Sep./Oct. 2007, vol. 16, No. 5S, pp. 267S-272S. (6 pages).
Wirth, Michael A., M.D. and Rockwood, Charles A., Jr., M.D., "Complications of Shoulder Arthroplasty," Clinical Orthopaedics and Related Research, Oct. 1994, No. 307, pp. 47-69. ( 23 pages).
Wirth, Michael A. and Rockwood, Charles A., Jr., "Current Concepts Review—Complications of Total Shoulder-Replacement Arthroplasty," Journal of Bone & Joint Surgery, Apr. 1996, vol. 78-A, No. 4, pp. 603-616. (15 pages).

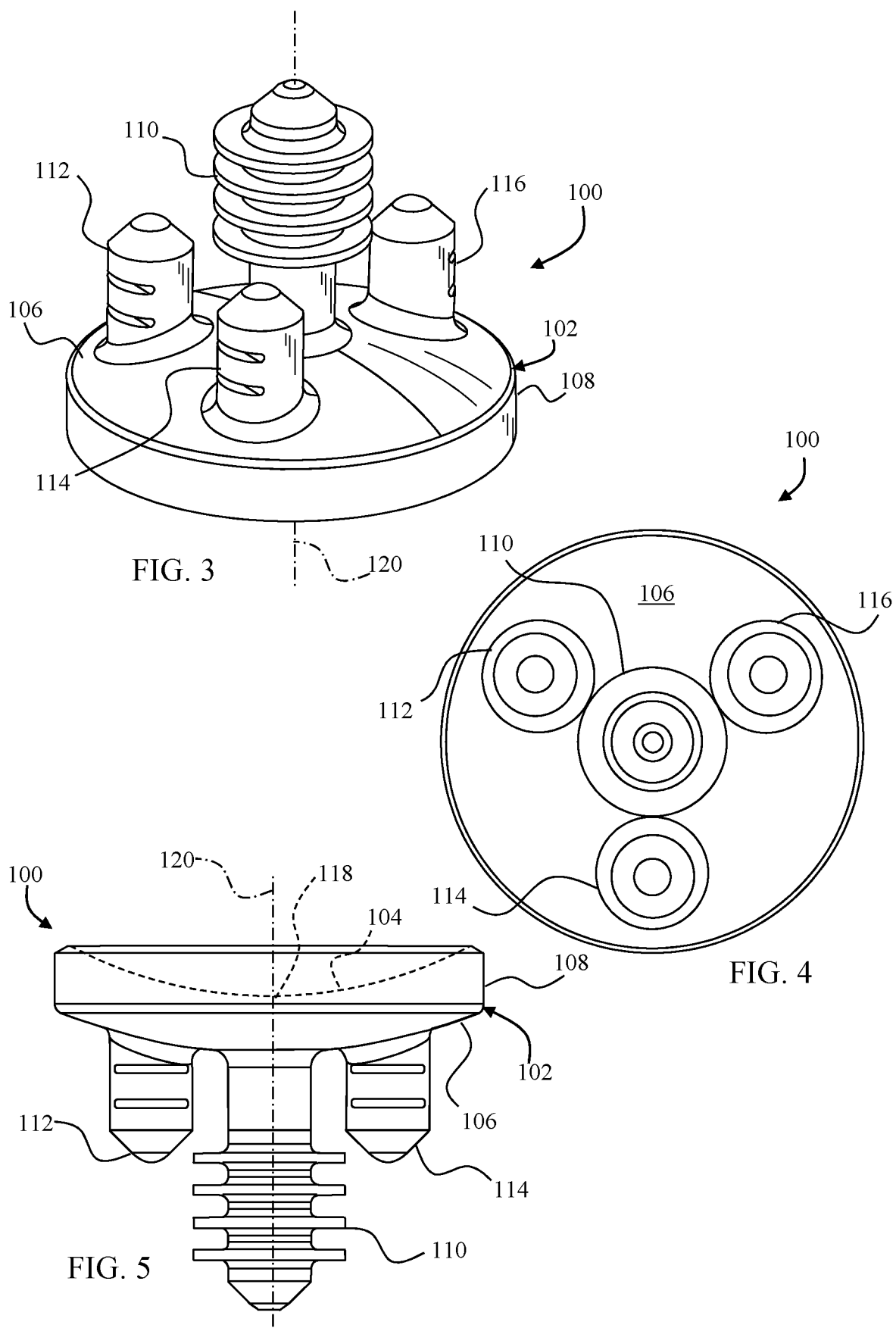

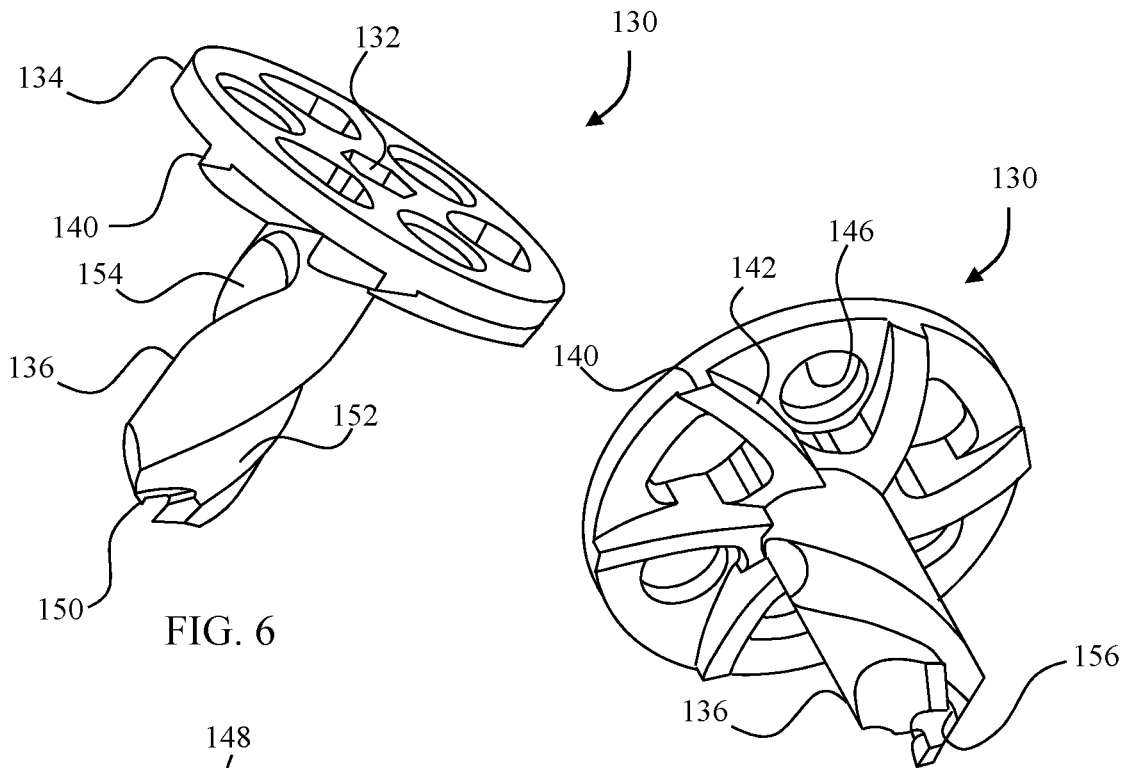
FIG. 6
FIG. 7
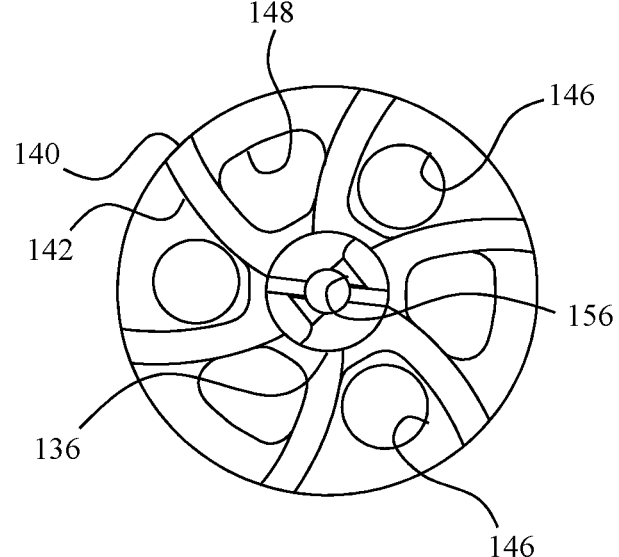
FIG. 8
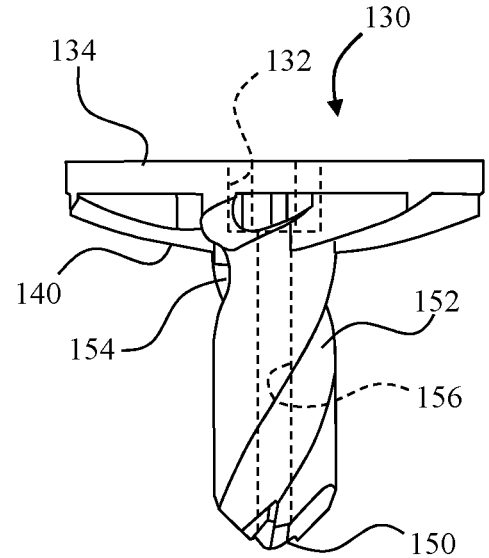
FIG. 9

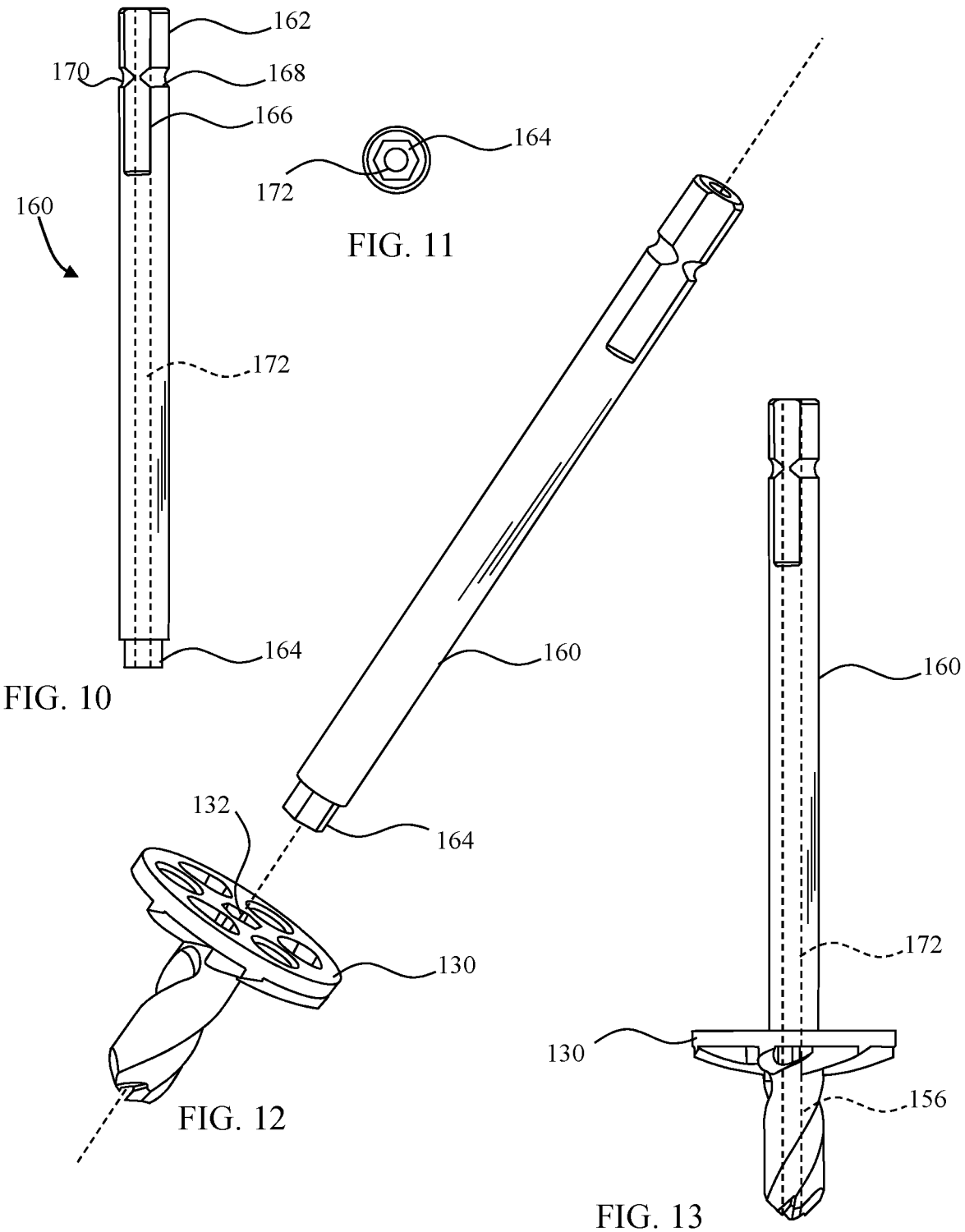

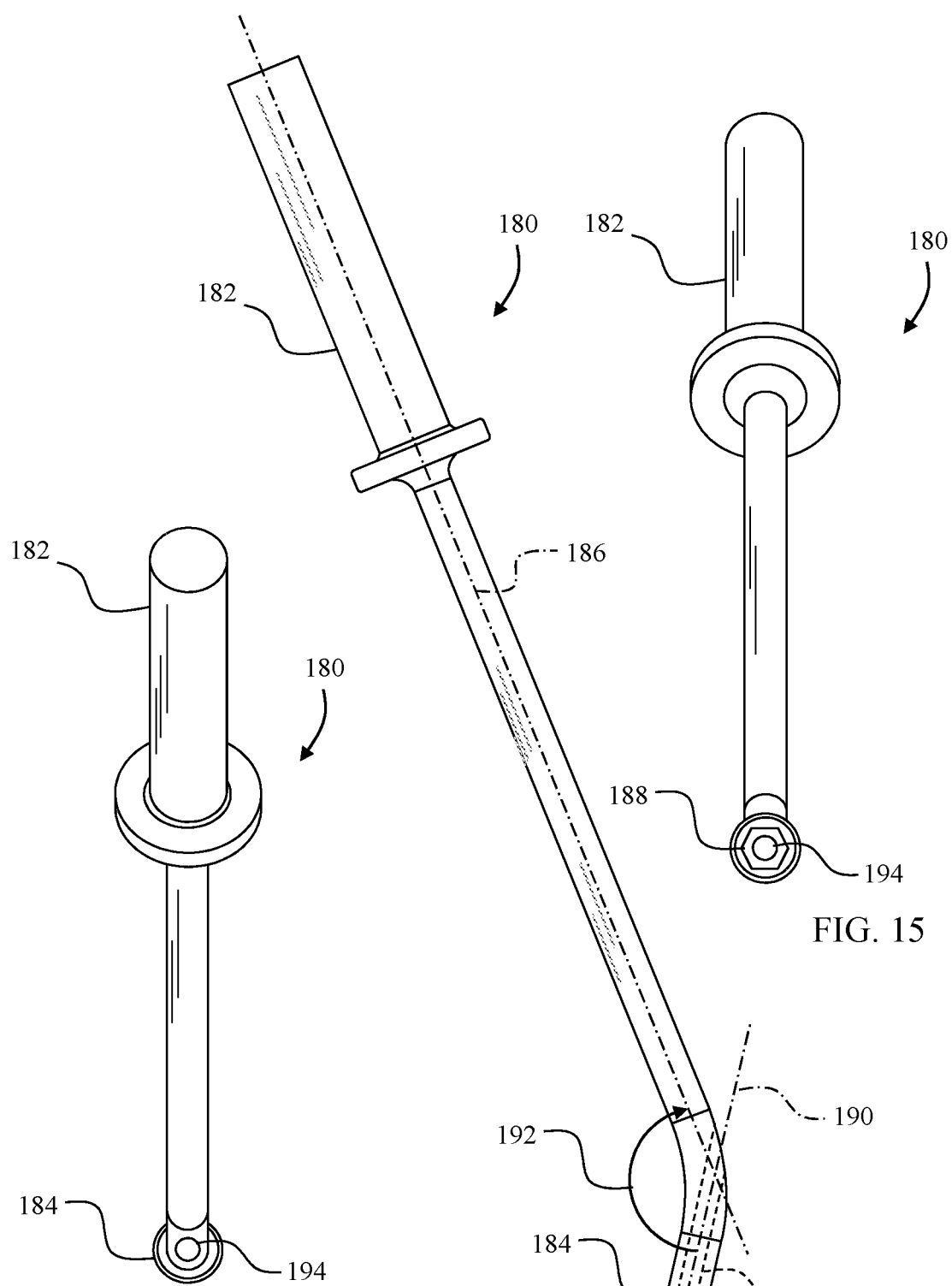

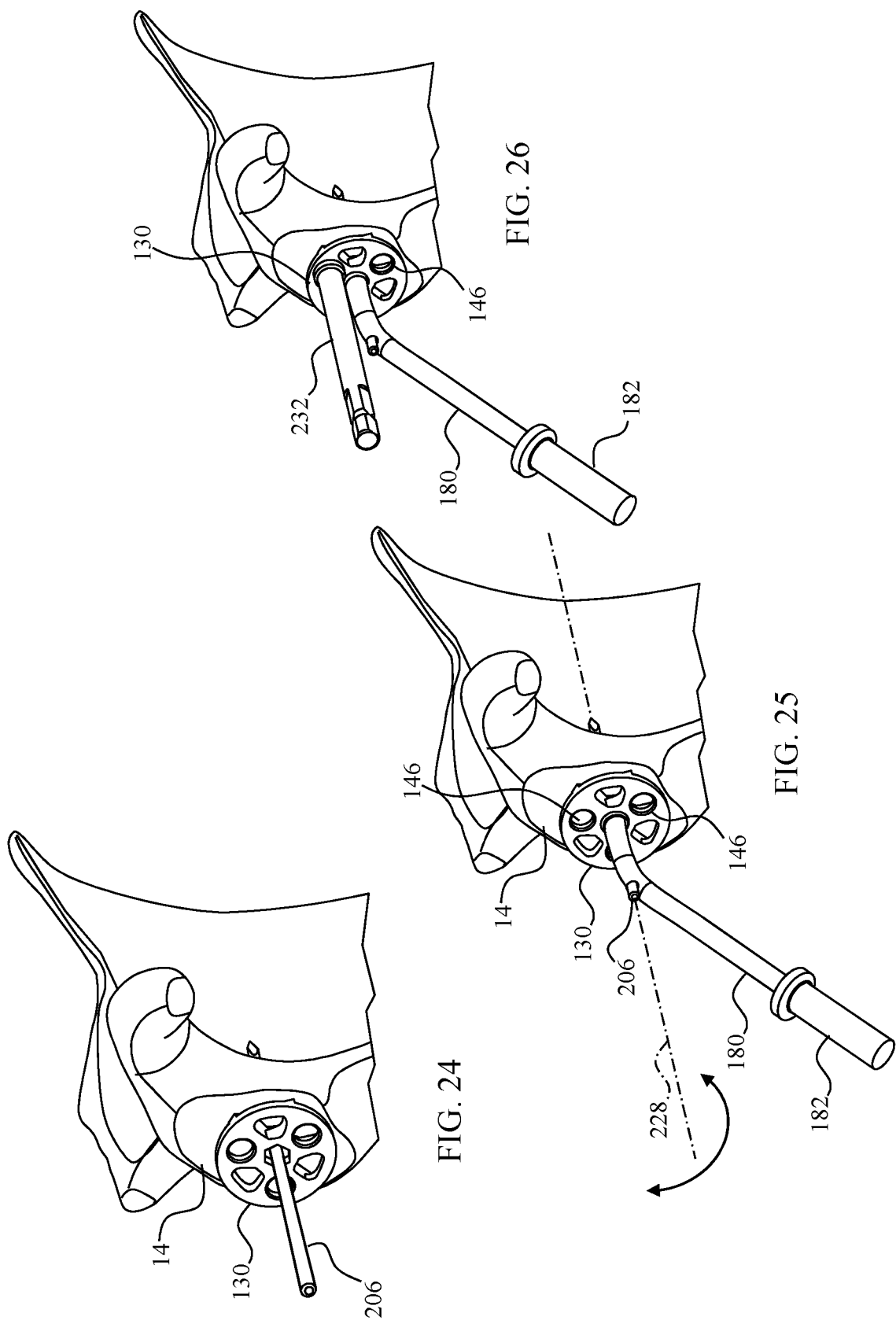

METHOD USING COMBINATION REAMER/DRILL BIT FOR SHOULDER ARTHROPLASTY

CROSS-REFERENCE TO RELATED APPLICATIONS

This application is a divisional application of copending U.S. application Ser. No. 13/051,026, entitled "Combination Reamer/Drill Bit for Shoulder Arthroplasty" filed Mar. 18, 2011, which issued on Nov. 21, 2017 as U.S. Pat. No. 9,820,758 and which is related to U.S. patent application Ser. No. 13/051,011, entitled "Circular Glenoid Method for Shoulder Arthroscopy", which was filed on Mar. 18, 2011 and issued as U.S. Pat. No. 8,764,836 on Jul. 1, 2014, U.S. patent application Ser. No. 13/051,041, entitled "Device and Method for Retroversion Correction for Shoulder Arthroscopy", which was also filed on Mar. 18, 2011 and issued as U.S. Pat. No. 9,226,830 on Jan. 5, 2016, and U.S. patent application Ser. No. 13/051,062, entitled "Revision Glenoid Device and Method", which was also filed on Mar. 18, 2011 and issued as U.S. Pat. No. 8,551,177 on Oct. 8, 2013, the contents of which are each incorporated herein by reference.

TECHNICAL FIELD OF THE INVENTION

The present invention relates generally to the field of orthopedics, and, more particularly, to glenoid component apparatuses for shoulder arthroplasty and methods for using them.

BACKGROUND

As depicted in FIG. 1, a typical shoulder or glenohumeral joint is formed in a human body where the humerus 10 movably contacts the scapula 12. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

Shoulder arthroplasty often involves replacement of the glenoid fossa of the scapula with a prosthetic glenoid component. The conventional glenoid component typically provides a generally laterally or outwardly facing generally concave bearing surface against which a prosthetic humeral head (or, alternatively, the spared natural humeral head in the case of a glenoid hemi-arthroplasty) may bear during operation of the joint. The conventional glenoid component typically also includes a generally medially or inwardly projecting stem for fixing the glenoid component in a cavity constructed by suitably resecting the glenoid fossa 14 and suitably resecting cancellous bone 22 from the glenoid vault 20.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical and positioning of the humeral component is accomplished by using the anatomical neck of the humerus as the reference plane for reconstruction of the humeral head.

Traditionally, shoulder joints have been understood to exhibit translation of the humeral component on the glenoid component in addition to rotation. Thus, the articulating surface of the glenoid is typically formed with a radius of curvature that is much larger than the radius of curvature of the humeral component. The increased radius of curvature of the glenoid articulating surface can be from 2-6 mm larger than the radius of curvature for the humeral component in these systems.

In known systems, the glenoid component is positioned in the geometric center of the glenoid fossa. The geometric center is established by generating a line from the most superior point of the glenoid rim to the most inferior point of the glenoid rim ("Saller's line"). A second line is generated between the most posterior point of the glenoid rim and the most anterior point of the glenoid rim. The intersection of the two generated lines is considered to be the geometric center of the area circumscribed by the glenoid rim. By way of example, FIG. 2 depicts a sagittal view of the scapula 12. In FIG. 2, Saller's line 30 extends between the most superior point 32 of the glenoid rim 24 to the most inferior point 34 of the glenoid rim 24. A second line 36 extends from the most posterior point 38 of the glenoid rim 24 and the most anterior point 40 of the glenoid rim. The geometric center 42 of the glenoid fossa 14 is located at the intersection of the line 36 and Saller's line 30. As used herein, the terms anterior, posterior, superior, and inferior, unless otherwise specifically described, are used with respect to the orientation of the scapula 12 as depicted in FIG. 2.

Once a surgeon determines the placement of the glenoid component, a guide pin is positioned through the glenoid fossa. A reamer is then used to shape the scapula to receive a glenoid component, typically by forming a cavity in the glenoid vault. For glenoid components including a center peg for fixation of the glenoid component within the glenoid vault, a bore is drilled using the guide pin as a guide. The guide pin is then removed. For glenoid components including offset pegs in addition to the center peg for fixation of the glenoid component within the glenoid vault, a drill guide is introduced into the prepared cavity and additional bores are drilled for each of the offset pegs. A trial glenoid component is then implanted in the prepared cavity and, if the fit appears to be satisfactory, the trial is removed and a glenoid component is implanted in the prepared cavity.

There exists a need for a simplified method of implanting a glenoid component. There is a further need for reducing the instrumentation required to properly prepare the scapula to receive a glenoid component.

SUMMARY OF THE INVENTION

The present invention in one embodiment provides an instrumentation kit for use in preparing a shoulder to receive a glenoid component which includes at least one combination device, the combination device including a boring section configured to rotationally form a first bore in a glenoid of a shoulder, a drive section operably connected to the boring section and configured to receive a rotational force, a reaming section positioned proximally from the boring section and operably connected to the drive section, the reaming section configured to rotationally ream a portion of the glenoid, and at least one drill guide configured to guide a drill bit and positioned so as to guide the drill bit to form a second bore in the shoulder at a location spaced apart from the first bore, wherein the reaming section and the boring section are positioned with respect to each other such that when the combination device is positioned against the glenoid and the rotational force is applied to the drive section, the boring section rotationally forms the first bore in the glenoid and the reaming section simultaneously rotationally reams a portion of the glenoid adjacent to the first bore.

In another embodiment, a method of preparing a shoulder to receive a glenoid component includes accessing a glenoid of a shoulder, applying a rotational force to a combination device, forming a first bore in the glenoid with a rotating boring section of the combination device, forming a second bore in the glenoid at a location spaced apart from the first bore using a first drill guide defined by the combination device, and reaming a portion of the glenoid with a rotating reaming section of the combination device, wherein forming a first bore and reaming a portion of the glenoid occur simultaneously.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

BRIEF DESCRIPTION OF THE DRAWINGS

FIG. 3 depicts a bottom perspective view of a circular glenoid component that may be implanted in a scapula in accordance with principles of the invention;

FIG. 4 depicts a bottom plan view of the circular glenoid component of FIG. 3;

FIG. 5 depicts a side plan view of the circular glenoid component of FIG. 3;

FIG. 6 depicts a side perspective view of a combination device that may be used to simultaneously form a bore for receiving a peg of a glenoid component and to ream a glenoid fossa to receive the glenoid component;

FIG. 7 depicts a bottom perspective view of the combination device of FIG. 6 showing the guide bore extending from a distal tip of the combination device;

FIG. 8 depicts a bottom plan view of the combination device of FIG. 6;

FIG. 9 depicts a side plan view of the combination device of FIG. 6 showing the guide bore extending to a drive section which in this embodiment is a hexagonally shaped bore in a body section of the combination device;

FIG. 10 depicts a side plan view of a power extension which may be used with the combination device of FIG. 6 to couple a power rotary tool (not shown) to the combination device;

FIG. 11 depicts a bottom plan view of the power extension of FIG. 10 showing a guide bore which extends from a distal tip of the power extension to a proximal tip of the power extension;

FIG. 12 depicts a perspective view of the combination device of FIG. 6 aligned with the power extension of FIG. 10;

FIG. 13 depicts a side plan view of the combination device of FIG. 6 coupled with the power extension of FIG. 10 such that the respective guide bores of the combination device and the power extension are aligned;

FIG. 14 depicts a side plan view of a manual extension which may be coupled with the combination device of FIG. 6 manually position the combination device;

FIG. 15 depicts a bottom plan view of the manual extension of FIG. 14 showing a guide bore which extends from a distal tip of the manual extension along an axis defined by the distal portion of the manual extension;

FIG. 16 depicts a top plan view of the manual extension of FIG. 14 showing the guide bore of FIG. 15;

FIG. 24 depicts a perspective view of the scapula of FIG. 23 after the power extension has been removed;

FIG. 25 depicts a perspective view of the scapula of FIG. 24 after the manual extension of FIG. 14 has been guided by the wire guide of FIG. 20 and coupled with the combination device of FIG. 6 allowing a user to manually orient the combination device on the scapula; and FIG. 26 depicts a perspective view of the scapula of FIG. 25 with the combination device of FIG. 6 used to guide a drill bit to form a bore to receive an offset peg of the glenoid component of FIG. 3 while the manual extension of FIG. 14 has been used to manually stabilize the combination device on the scapula.

DETAILED DESCRIPTION

Figure 1:
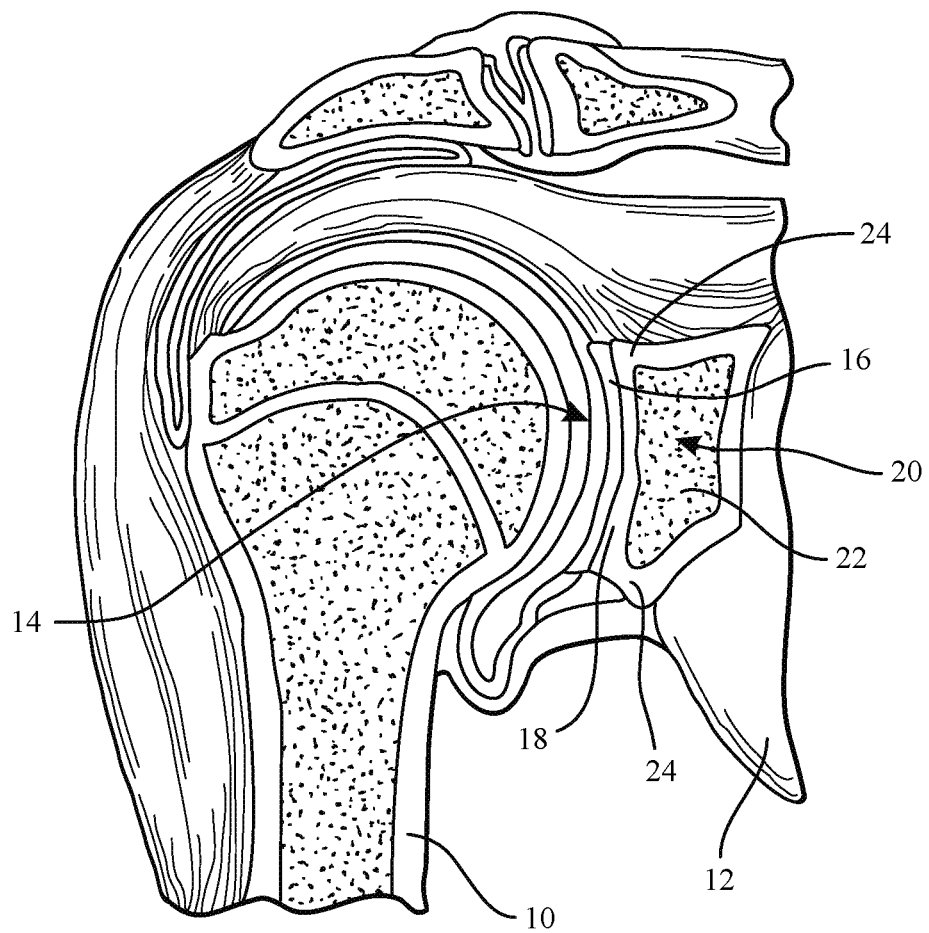
FIG. 1 depicts a coronal view of an anatomically normal shoulder joint.
Figure 2:
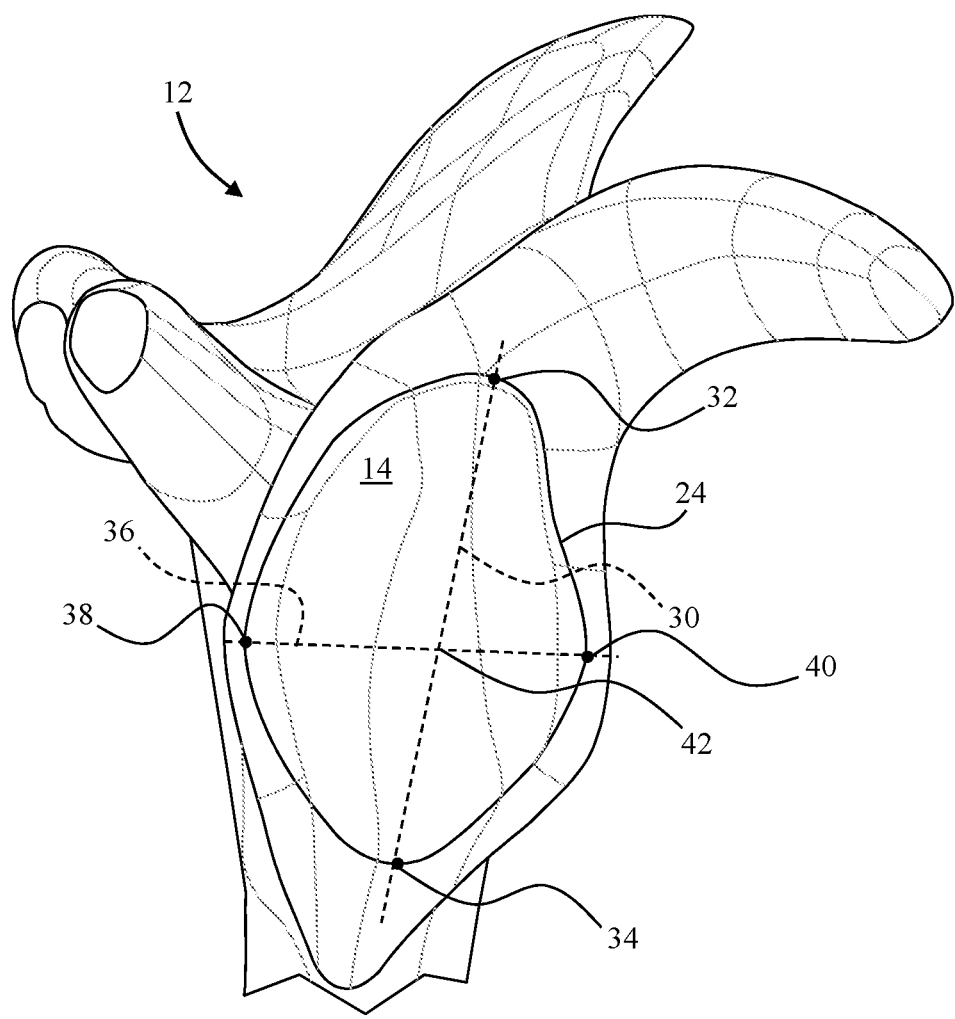
FIG. 2 depicts a sagittal view of the shoulder joint of FIG. 1.

Like reference numerals refer to like parts throughout the following description and the accompanying drawings.

FIGS. 3-5 depict a glenoid component 100. The glenoid component 100 includes a body portion 102 including a spherical articulating surface 104 and an opposite bone contacting surface 106. An outer wall 108 extends away from the bone contacting surface 106 and defines an outer periphery of the body portion 102. The bone contacting surface 106 is generally convex. A finned center peg 110 extends away from the nadir of the bone contacting surface 106 as viewed in FIG. 5. Three offset pegs 112, 114, and 116 extend away from the bone contacting surface 106 at locations between the center peg 110 and the outer wall 108. The nadir 118 of the spherical articulating surface 104 is located on the centerline 120 of the glenoid component 100.

The glenoid component 100 in this embodiment is an integrally formed unit made from a durable biocompatible plastic or any other suitable durable biocompatible material. For example, the glenoid component 100 may be made from a polyethylene. One particular polyethylene that is well suited for glenoid component 100 is a high molecular weight polyethylene, for example ultra-high molecular weight polyethylene ("UHMWPE"). One such UHMWPE is sold as by Johnson & Johnson of New Brunswick, N.J. as MARATHON™ UHMWPE and is more fully described in U.S. Pat. Nos. 6,228,900 and 6,281,264 to McKellop, which are incorporated herein by reference.

In embodiments wherein the articulating surface 104 and the other portions of the glenoid component 100 are made from different materials, the portions of the glenoid component 100 other than the articulating surface 104 may be made from a suitable biocompatible metal such as, for example, a cobalt chromium alloy, a stainless steel alloy, a titanium alloy, or any other suitable durable material. In these embodiments, the articulating surface 104 is secured to the body portion 102 in any suitable manner. For example, articulating surface 104 may be bonded to body portion 102, or articulating surface 104 could be made from polyethylene and compression molded to body portion 102. Alternately, the articulating surface 104 may be glued to the body portion 102 by, for example, an adhesive. Alternatively, articulating surface 104 may be mechanically interlocked to the body portion 102 by taper locking or otherwise press-fitting the articulating surface 104 into the body 102 and the body 102 may include any other suitable interlocking features, for example, rib(s), lip(s), detent(s), and/or other protrusion(s) and mating groove(s), channel(s), or indent(s) (not shown).

In alternative embodiments, one or more of the outer wall 108, the bone contacting surface 106, the center peg 110 and the offset pegs 112, 114, and 116 may include a porous coating to facilitate bone in-growth into the glenoid component 100. The porous coating may be any suitable porous coating and may for example be POROCOAT®, a product of Johnson & Johnson of New Brunswick, N.J. and more fully described in U.S. Pat. No. 3,855,638 to Pilliar, which is incorporated herein by reference.

In order to implant the glenoid component 100 into a scapula, the scapula must first be prepared to receive the glenoid component 100. A device which can be used to prepare the scapula to receive the glenoid component 100 is depicted in FIGS. 6-9. With reference to FIGS. 6-9, a combination device 130 includes a drive section 132, a body section 134, and a drill or boring section 136. The drive section 132 in this embodiment is a hexagonally shaped bore defined in the body section 134.

A number of reaming fins 140 extend from the lower central portion of the body section 134 toward the drill section 136. The reaming fins 140 curve proximally and outwardly from the lower central portion of the body section 134 to the outer periphery of the body section 134. The reaming fins 140 include an arcuate leading edge 142. The body section 134 defines a number of through-holes at locations between adjacent reaming fins 140. The through-holes in the embodiment of FIGS. 6-9 include three drill guides 146 and three ports 148.

The drill section 136 extends away from the body section 134 to a distal tip 150. Two flutes 152 and 154 extend helically about the drill section 136 between the body section 134 and the distal tip 150. A guide bore 156 extends from the distal tip 150 to the drive section 132.

As discussed in further detail below, a kit may include one or more combination devices 130 along with various instrumentation to facilitate use of the combination device 130. By way of example, FIG. 10 depicts a power extension 160 that may be included in the kit. The power extension 160 includes a power receiving portion 162 and a power transfer portion 164. The power receiving portion 162 is sized and configured to couple with a power tool and includes a pair of opposing power receiving flats 166 and a pair of coupling grooves 168 and 170 which extend about the power receiving portion 162 between the power receiving flats 166.

The power transfer portion 164 is shaped to be complimentary to the drive section 132. In the embodiment of FIGS. 10 and 11, the power transfer portion 164 is thus a hexagonally shaped protrusion sized to fit within the drive section 132. A guide bore 172 extends from the distal tip of the power transfer portion 164 to the proximal end of the power receiving portion 162.

To couple the combination device 130 with the power extension 160, the power transfer portion 164 is aligned with the drive section 132 as shown in FIG. 12. The combination device 130 with the power extension 160 are then moved toward each other such that the power transfer portion 164 enters into the drive section 132 resulting in the configuration of FIG. 13. In FIG. 13, the guide bore 156 of the combination device 130 is aligned with the guide bore 172 of the power extension 160.

FIGS. 14-16 depict a manual extension 180 that may also be included in the kit. The manual extension 180 includes a handle portion 182 and a power transfer portion 184. The handle portion 182 is sized and configured to be easily gripped and defines a first axis 186.

The power transfer portion 184 includes a hexagonal protuberance 188 shaped to be complimentary to the drive section 132. The power transfer portion 184 defines a second axis 190. The second axis 190 forms an angle 192 of about 145 degrees with the first axis 186. A guide bore 194 extends from the distal tip of the power transfer portion 184 along the second axis 190.

Figures 17, 18:
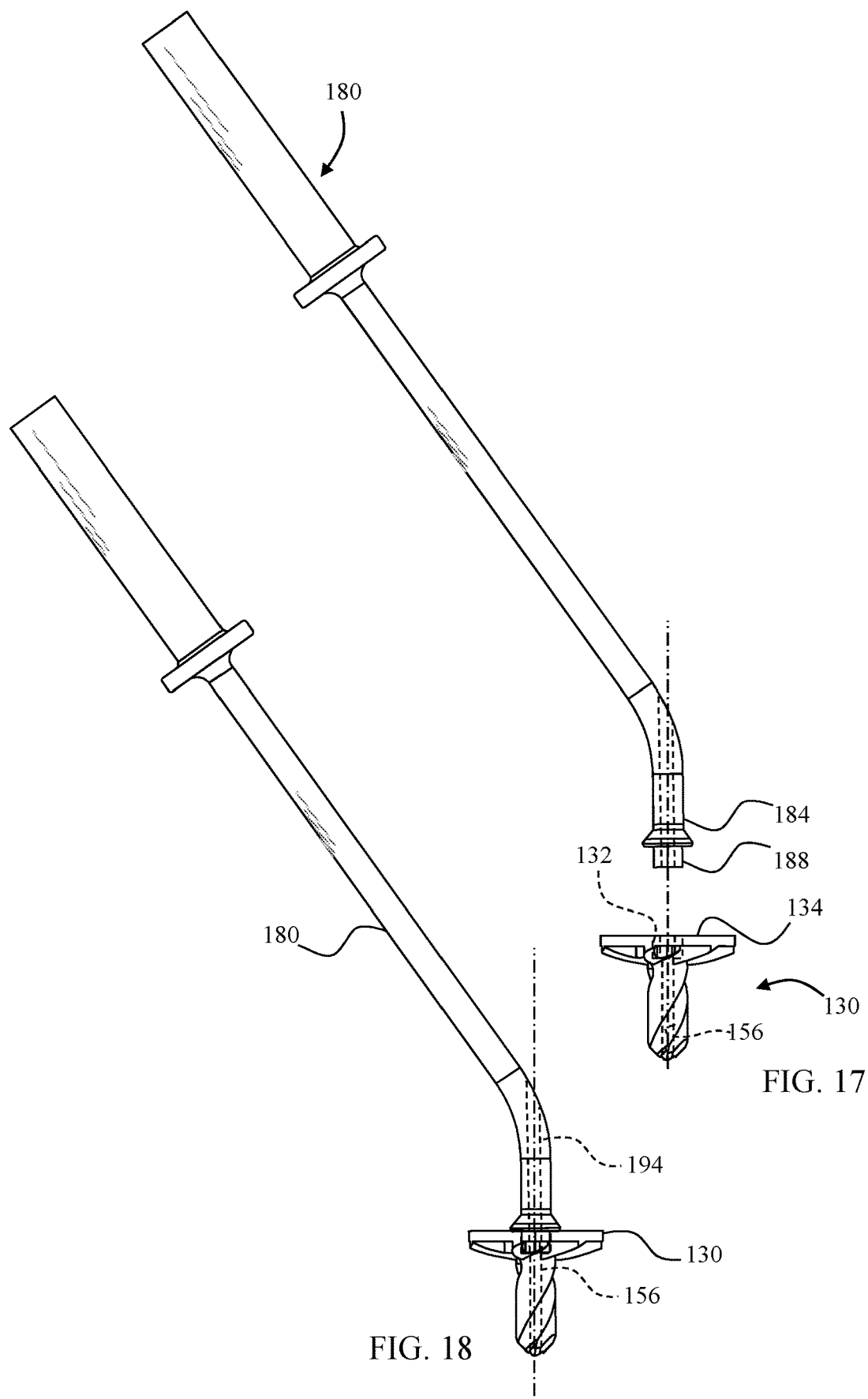
FIG. 17 depicts a side plan view of the combination device of FIG. 6 aligned with the manual extension of FIG. 14.
FIG. 18 depicts a side plan view of the combination device of FIG. 6 coupled with the manual extension of FIG. 14 0 such that the respective guide bores of the combination device and the manual extension are aligned.

To couple the combination device 130 with the manual extension 180, the power transfer portion 184 is aligned with the drive section 132 as shown in FIG. 17. The combination device 130 and the manual extension 180 are then moved toward each other such that the hexagonal protuberance 188 enters into the drive section 132 resulting in the configuration of FIG. 18.

In FIG. 18, the guide bore 156 of the combination device 130 is aligned with the guide bore 194 of the manual extension 180. Beneficially, the angle 192 (see FIG. 14) between the handle portion 182 and the power transfer portion 184 allows a user to easily see the guide bore 194, thereby assisting in alignment of the power transfer portion 184 with the drive section 132 or, as discussed in more detail below, with a guide wire extending through the guide bore 156. The angle 192 further provides a mechanical advantage in maintaining the combination device 130 in a desired location as also discussed below.

Figure 19:
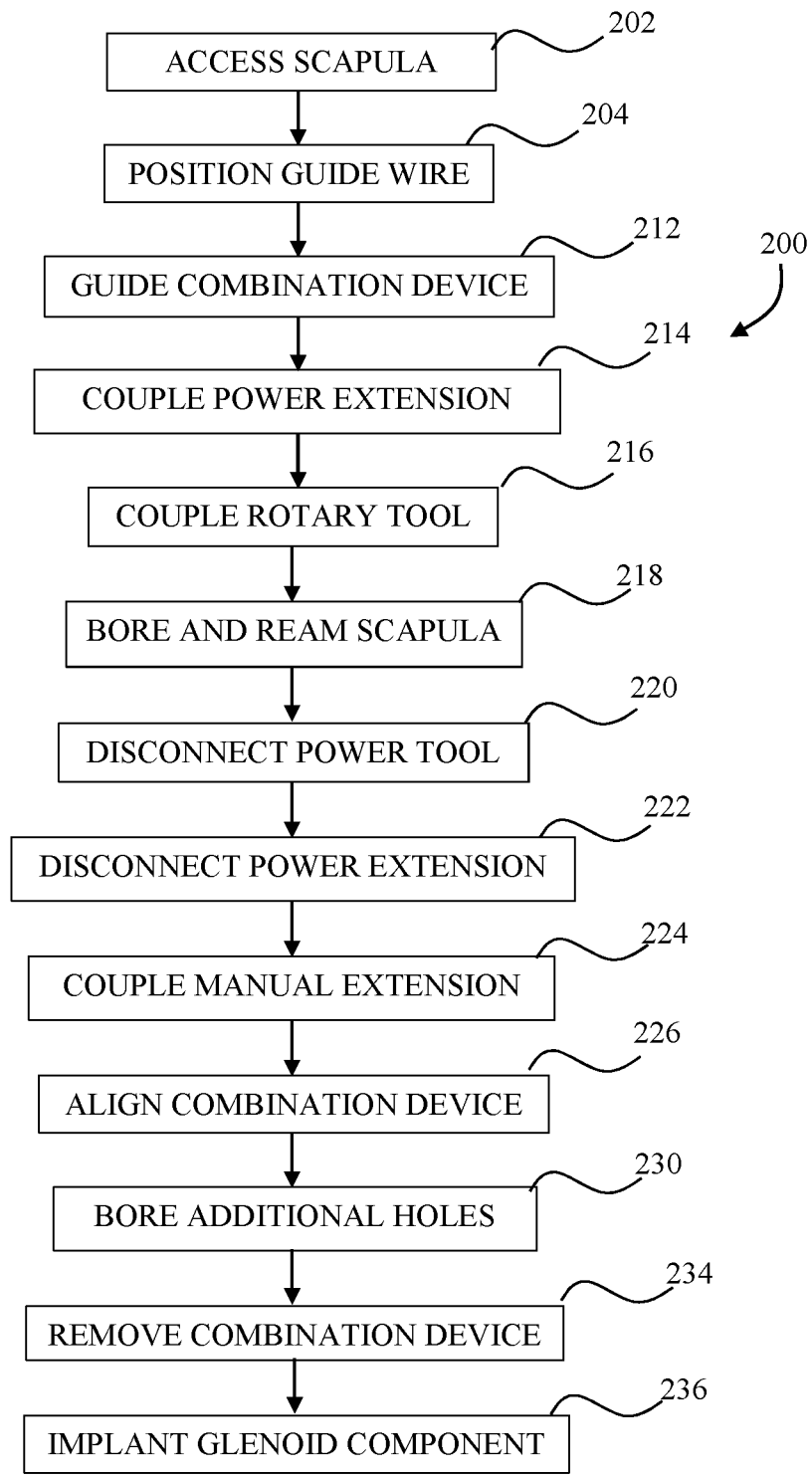
FIG. 19 depicts a medical procedure that may be used to implant the circular glenoid component of FIG. 3 into a scapula using the combination device of FIG. 6.
Figure 20:
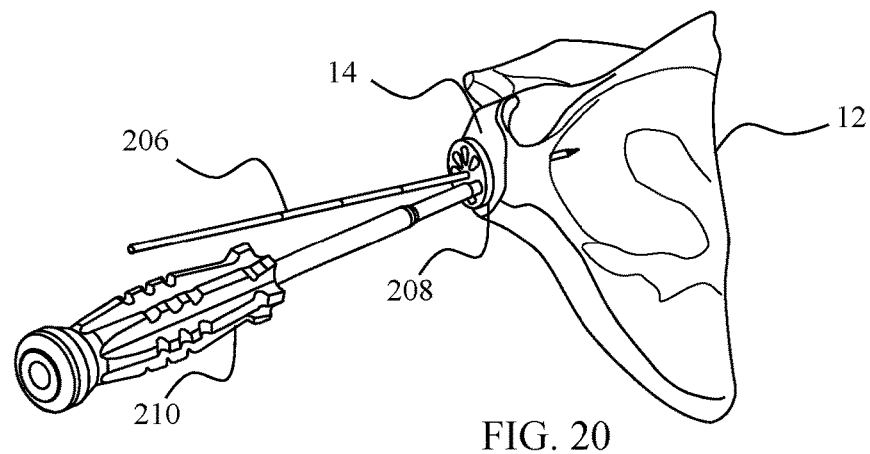
FIG. 20 depicts a perspective view of the scapula of FIG. 2 with a guide wire positioned in the scapula using a guide template and a guide template manipulator.

A kit including the combination device 130, the power extension 160, and the manual extension 180 may be used in preparing a shoulder to receive a glenoid component such as glenoid component 100 in accordance with a procedure 200 depicted in FIG. 19. Initially, a scapula is accessed at block 202 in accordance with a desired surgical approach. At block 204, a guide wire, which may be provided in a kit along with other instrumentation used in the procedure 200, is positioned on the scapula. Positioning of the guide wire may be computer aided. In one embodiment, the guide wire is positioned based upon identification of the center of an inferior glenoid circle. By way of example, FIG. 20 depicts a guide wire 206 implanted into a glenoid 14 of the scapula 12. In the embodiment of FIG. 20, the guide wire 206 has been positioned with the aid of a guide plate 208 and a guide plate manipulator 210.

Figure 21:
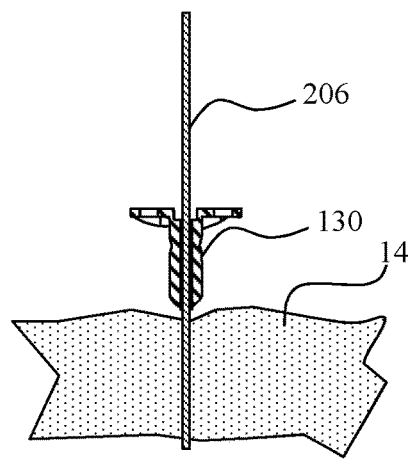
FIG. 21 depicts a partial cross-sectional view of the scapula of FIG. 20 with the combination device of FIG. 6 guided to a location adjacent to the glenoid fossa by the guide wire of FIG. 20.

Once the guide wire is positioned, a combination device 130 is positioned with the guide bore 156 aligned with the guide wire. The combination device 130 is then moved toward the guide wire and at block 212 the guide wire is used to guide the combination device 130 to a location adjacent to the glenoid 14 of the scapula 12 as depicted in FIG. 21.

Figure 22:
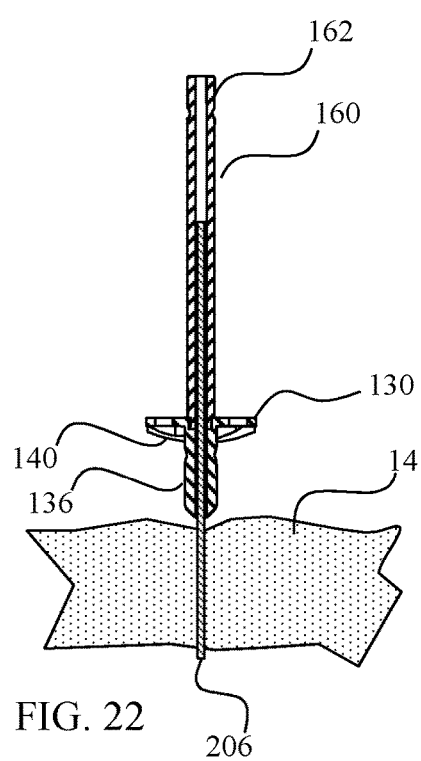
FIG. 22 depicts a partial cross-sectional view of the scapula of FIG. 20 with the power extension of FIG. 10 coupled to the combination device of FIG. 6, both the power extension and the combination device guided to a location adjacent to the glenoid fossa by the guide wire of FIG. 20.

At block 214, a power extension 160 is coupled to the combination device 130 substantially in the manner described above. Since the guide wire 206 extends through the guide bore 156 of the combination device 130, however, coupling of the power extension 160 to the combination device 130 begins by aligning the guide bore 172 of the power extension 160 with the guide wire 206. The guide wire 206 thus guides the power extension 160 to the combination device 130. Some rotation of the power extension 160 may be required to align the power transfer portion 164 with the drive section 132 of the combination device 130 to allow coupling of the power extension 160 with the combination device 130. The resulting configuration is depicted in FIG. 22.

A rotary tool (not shown) is then coupled to the combination device 130 at block 216. In some embodiments, a rotary tool may be directly coupled to the combination device 130. In this example, the power extension 160 is coupled to the combination device 130 as described above. Thus, the rotary tool is coupled to the power receiving portion 162 of the power extension 160 so as to be indirectly coupled to the combination device 130.

Figure 23:
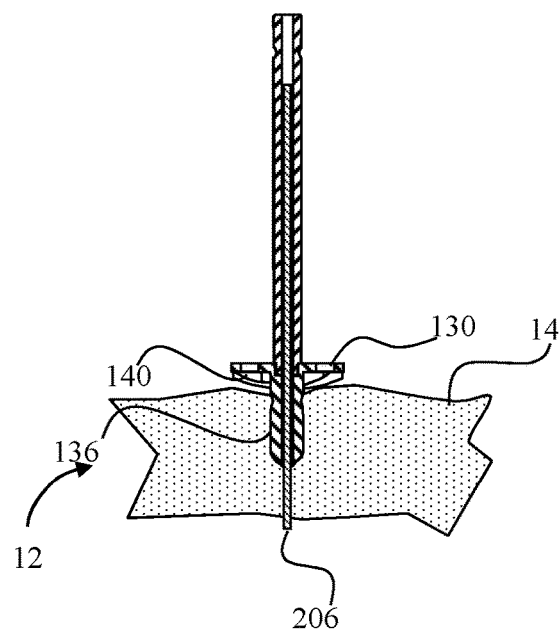
FIG. 23 depicts a partial cross-sectional view of the scapula of FIG. 20 and the coupled power extension and combination device of FIG. 22 after the combination device has been used to simultaneously ream the glenoid fossa and form a bore in preparation for implanting the glenoid component of FIG. 3 into the scapula.

Power is then applied to the rotary tool causing the rotary tool to rotate the power extension 160. Rotary force is transferred to the drive section 132 of the combination device 130 through the power transfer portion 164 (see FIG. 12). As the combination device 130 initially rotates about the guide wire 206, the drill section 136 contacts the glenoid 14 and begins to bore a hole in the glenoid 14. The reaming fins 140, however, are initially spaced apart from the glenoid 14 as depicted in FIG. 22. Accordingly, no reaming occurs. As a hole is formed in the glenoid 14 by the drill section 136, the combination device 130 is guided by the guide wire such that the reaming fins 140 come into contact with the glenoid 14 as depicted in FIG. 23. Continued rotation of the combination device 130 with the rotary tool thus causes simultaneous reaming of the glenoid 14 with the reaming fins 140 and boring of the scapula 12 with the drill section 136 at block 218.

Once the glenoid 14 has been reamed to the desired depth, the power tool is de-energized and disconnected at block 220. The size of the drill section 132, both in length and diameter, is selected to be complimentary to the size of the center peg 110 of the glenoid component 100. Thus, upon completion of the reaming, the bore formed by the drill section is sized to receive the finned center peg 110. The power extension 160 is disconnected at block 222, resulting in the configuration of FIG. 24.

At block 224, the manual extension 180 is coupled to the combination device 130 substantially in the manner described above. Since the guide wire 206 extends through the guide bore 156 of the combination device 130, however, coupling of the manual extension 180 to the combination device 130 begins by aligning the guide bore 190 of the manual extension 180 with the guide wire 206. The guide wire 206 thus guides the manual extension 180 to the combination device 130. Some rotation of the manual extension 180 may be required to align the hexagonal protuberance 188 of the manual extension 180 with the drive section 132 of the combination device 130 to allow coupling of the manual extension 180 with the combination device 130. The resulting configuration is depicted in FIG. 25.

Once the manual extension 180 has been coupled with the combination device 130, the manual extension 180 may be used to align the combination device 130 at block 226 as explained with reference to FIG. 25. Specifically, the handle portion 182 may be rotated about the axis 228 defined by the guide wire 206. Rotation of the handle portion 182 about the axis 228 causes rotation of the combination device 130 about the axis 228.

The curvature of the manual extension 180 resulting from the angle 192 (see FIG. 14) provides a surgeon with a relatively unobstructed view of the combination device 130. Accordingly, the surgeon may view the reamed surface of the glenoid 14 through the drill guides 146. This allows a surgeon to view the location in the shoulder 12 at which the offset fixation pegs 112, 114, and 116 of the glenoid component 100 will be anchored. In the embodiments in this example wherein the number and positioning of the drill guides 146 are complimentary to the number and positioning of the offset fixation pegs 112, 114, and 116, such that the drill guide axes are parallel to a boring axis of the boring section 136, the surgeon may orient the combination device 130 such that each of the drill guides 146 is aligned with portions of the shoulder that can provide a good anchor for the offset fixation pegs 112, 114, and 116.

Once the combination device 130 is aligned at the block 226, a drill bit is inserted through one of the drill guides 146 to drill an additional bore at a location spaced apart from the first bore formed using the drill section 136 at block 230. By way of example, FIG. 26 depicts a drill bit 232 positioned in a first circular drill guide 146 of the combination device 130. The manual extension 180 may be used to steady the combination device 130 during the drilling process. The offset of the handle portion 182 from the axis 228 provided by the angle 192 results in a mechanical advantage in maintaining the combination device 130 at the desired orientation. Blocks 226 and 230 may be repeated as desired to form additional holes through, e.g., a second circular drill guide 146.

Once all of the desired holes are formed, the combination device 130 is removed at block 234. The manual extension 180 may be used to aid in removal of the combination device 130. At block 236, the glenoid component is implanted. In this example, the glenoid component 100 has a lower bone contacting surface 106 shaped complimentary to the reaming cross-section of the reaming fins 140. Thus, in this example the lower bone contacting surface 106 is curved complimentary to the distal curve of the reaming fins 140. In other embodiments, the reaming fins 140 may be configured to produce a flat bottomed area if a glenoid component with a flat lower bone contacting surface is used. Accordingly, a kit may include different combination devices with differently shaped reaming cross-sections.

The combination device 130 and the procedure 200 may be used in combination with various of the devices and procedures disclosed in the related applications identified above. Thus, while the combination device 130 is useful in implanting a circular glenoid device at the center of the inferior glenoid circle, the combination device 130 may be used to implant other glenoid components, including non-circular glenoid components, at any desired location in a glenoid. Preferably, the diameter of the reaming cross-section of the combination device 130 is selected to match the largest diameter of a glenoid component. Thus, while a kit may include one or more combination devices 130 of the same reaming diameter, a kit may alternatively include a number of combination devices with differently sized reaming diameters.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method of preparing a shoulder to receive a glenoid component comprising:
   accessing a glenoid of a shoulder;
   applying a rotational force to a combination device;
   forming a first bore in the glenoid with a rotating boring section of the combination device;
   forming a second bore in the glenoid at a location spaced apart from the first bore using a first drill guide defined by the combination device; and
   reaming a portion of the glenoid with a rotating reaming section of the combination device, wherein as the first bore is being formed, continued rotation of the combination device causes the rotating reaming section of the combination device to come into contact with the portion of the glenoid such that the reaming of the portion of the glenoid occurs simultaneously with a part of the step of forming the first bore.

2. The method of claim 1, wherein forming the second bore comprises:
   extending a drill bit through the first drill guide, wherein the first drill guide is circular and formed in a body portion of the combination device and between a first and a second reaming fin, the first and second reaming fins extending distally from the body portion.

3. The method of claim 2, wherein reaming the portion of the glenoid comprises:
   reaming a portion of the glenoid with the rotating reaming section of the combination device including a plurality of reaming fins each defining an arcuate leading edge.

4. The method of claim 2, wherein extending the drill bit through the first circular drill guide comprises:
   extending the drill bit through the first circular drill guide along a drill guide axis that is parallel to a boring axis of the boring section.

5. The method of claim 2, further comprising:
   forming a third bore by extending the drill bit through a second circular drill guide formed in the body portion of the combination device and between a third and a fourth reaming fin, the third and fourth reaming fins extending distally from the body portion.

6. The method of claim 5, wherein:
   extending the drill bit through the first circular drill guide comprises extending the drill bit through the first circular drill guide along a drill guide axis that is parallel to a boring axis of the boring section; and
   forming the third bore comprises extending the drill bit through the second circular drill guide along a second drill guide axis that is parallel to the boring axis of the boring section.

7. The method of claim 1, further comprising:
   positioning a guide wire in the glenoid;
   aligning a guide bore in the combination device with the positioned guide wire; and
   after aligning the guide bore in the combination device with the positioned guide wire, moving the combination device toward the positioned guide wire and into contact with the glenoid such that reaming the portion of the glenoid occurs with a portion of the guide wire positioned in the guide bore.

8. The method of claim 7, further comprising:
   coupling a power extension with the combination device with the portion of the guide wire positioned in the guide bore;
   rotating the combination device with the power extension with the portion of the guide wire positioned in the guide bore; and
   removing the power extension after reaming the portion of the glenoid and before forming the second bore.

9. The method of claim 8, further comprising:
   coupling a manual extension with the combination device after removing the power extension and before forming the second bore.

10. The method of claim 9, wherein coupling the manual extension comprises:
    aligning a guide bore in the manual extension with the positioned guide wire; and
    after aligning the guide bore in the manual extension with the positioned guide wire, moving the manual extension toward the positioned guide wire and into contact with the combination device.

11. The method of claim 10, wherein moving the manual extension toward the positioned guide wire comprises:
    moving the manual extension toward the positioned guide wire using a handle portion of the manual extension which is not aligned with the positioned guide wire.

12. The method of claim 9, wherein:
    coupling the power extension with the combination device with the portion of the guide wire positioned in the guide bore comprises coupling the power extension with a drive section of the combination device; and
    coupling the manual extension with the combination device after removing the power extension and before forming the second bore comprises coupling the manual extension with the drive section of the combination device.

13. The method of claim 1, further comprising:
    selecting the combination device from a kit including a plurality of combination devices, each of the plurality of combination devices defining a reaming diameter different from the reaming diameters of the others of the plurality of combination devices.

* * * * *